United States Patent
Kataoka et al.

(10) Patent No.: US 7,125,546 B2
(45) Date of Patent: Oct. 24, 2006

(54) POLYMERIC MICELLE CONTAINING CISPLATIN ENCLOSED THEREIN AND USE THEREOF

(75) Inventors: Kazunori Kataoka, Tokyo (JP); Nobuhiro Nishiyama, Tokyo (JP); Masayuki Yokoyama, Chiba (JP); Teruo Okano, Ichikawa (JP)

(73) Assignee: Toudai TLO, Ltd., Tokyo (JP)

( * ) Notice: Subject to any disclaimer, the term of this patent is extended or adjusted under 35 U.S.C. 154(b) by 416 days.

(21) Appl. No.: 10/381,339

(22) PCT Filed: Sep. 26, 2001

(86) PCT No.: PCT/JP01/08337

§ 371 (c)(1), (2), (4) Date: May 5, 2003

(87) PCT Pub. No.: WO02/26241

PCT Pub. Date: Apr. 4, 2002

(65) Prior Publication Data

US 2003/0170201 A1  Sep. 11, 2003

(30) Foreign Application Priority Data

Sep. 26, 2000 (JP) ............................. 2000-292218

(51) Int. Cl.
*A61K 47/48* (2006.01)
*A61K 31/74* (2006.01)
*A61K 9/14* (2006.01)
*A61K 33/24* (2006.01)
*A61K 31/282* (2006.01)
*A61K 47/32* (2006.01)
*A61K 31/28* (2006.01)
*A01N 59/26* (2006.01)
*A01N 55/02* (2006.01)

(52) U.S. Cl. ................ 424/78.17; 424/78.08; 424/489; 424/604; 514/492; 514/772.6

(58) Field of Classification Search .............. 424/8.08, 424/78.17, 450, 489, 604, 649, 78.08; 514/492, 514/772.6
See application file for complete search history.

(56) References Cited

U.S. PATENT DOCUMENTS 5,384,333 A   1/1995   Davis et al.
5,449,513 A * 9/1995   Yokoyama et al. ...... 424/78.08

FOREIGN PATENT DOCUMENTS

| EP | 0 397 307 | 11/1990 |
| EP | 397307 | 11/1990 |
| EP | 583955 | 2/1994 |
| JP | 5-955 | 1/1993 |
| JP | 5-117385 | 5/1993 |

OTHER PUBLICATIONS

B. Schechter et al., "Increased Therapeutic Efficacy of Cis-Platinum Complexes of Poly-L-Glutamic Acid Against A Murine Carcinoma", International Journal of Cancer, vol. 39, No. 3, pp. 409-413, 1987.
S. R. Meshnick et al., "Capacity of a Cis-Diammineplatium [II]-Poluglutamic Acid Complex to Cure Trypanosoma Congolense Infections in Mice", vol. 25, No. 2, pp. 286-288, Feb. 1984.
M. Yokoyama et al., "Introduction of cisplatin into polymeric micelle", Journal of Controlled Release, vol. 39, pp. 351-356, 1996.
N. Nishiyama et al., "Preparation and Characterization of Self-Assembled Polymer-Metal Complex Micelle from cis-Dichlordiammineplatinum(II) and Poly(ethylene glycol)-Poly($\alpha,\beta$-aspartic acid) Block Polymer in an Aqueous Medium", Langmuir, vol. 15, No. 2, pp. 377-383, 1999.
K. Kataoka, "Nanoparticle formulation from polymeric micelles", Pharm Tech Japan, vol. 16, No. 8, 2000, pp. 1209-1219 and its partial English translation.

* cited by examiner

*Primary Examiner*—Johann Richter
(74) *Attorney, Agent, or Firm*—Wenderoth, Lind & Ponack, L.L.P.

(57) ABSTRACT

Provided is a complex comprising cisplatin encapsulated therein in a form in which a chlorine ion thereof is ligand-exchanged with a carboxyl anion of a block copolymer comprising poly(ethylene glycol)-poly(glutamic acid). This complex can be a medicinal preparation to which a novel dosage form decreased in toxicity can be applied.

21 Claims, 5 Drawing Sheets

Fig.1

(a) PEG-P(Glu) 5-35

(b) PEG-P(Glu) 12-35

(c) PEG-P(Glu) 12-70

(A) Blood plasma

PEG-(Asp)

PEG-(Glu)

(B) Tumor (C) Kidney

Fig.4

(D) Liver (E) Spleen

Fig.5

(A) Relative antitumor effect (B) Relative body weight change (C) Relative BUN value change

POLYMERIC MICELLE CONTAINING CISPLATIN ENCLOSED THEREIN AND USE THEREOF

This application is a U.S. national stage of International Application No. PCT/JP01/08337 filed Sep. 26, 2001.

TECHNICAL FIELD

The present invention relates to a complex of a copolymer (hereinafter abbreviated as PEG-P(Glu)) comprising a poly (ethylene glycol) segment (hereinafter abbreviated as PEG) and a poly($\alpha$-glutamic acid) segment (hereinafter abbreviated as P(Glu)) with cisplatin and a medicine comprising the above complex as an effective ingredient.

BACKGROUND ART

Cisplatin (cis-Diaminedichloroplatinum (II); hereinafter abbreviated as CDDP) is a very effective carcinostatic agent in a medical practice, but it is known that it has very strong side effects such as nephrotoxicity. Further, when CDDP is administered in blood, it is quickly excreted to the outside of the body by glomerular filtration, and therefore the blood half-time thereof is very short. Accordingly, a lot of pharmaceutical preparations have so far been tried to be developed by many researchers in order to extend this blood half-time of CDDP and reduce nephrotoxicity, but the existing situation is that the successful examples thereof have not yet been achieved.

Thus, it is the existing situation that in general, a suitable transfusion is administered before administering a CDDP agent and that CDDP is then mixed with a large amount of a physiological salt solution or a glucose-salt solution and it is intravenously dripped in several hours.

Accordingly, strongly desired to be developed is a pharmaceutical preparation which makes it possible to carry out a new administering form in place of complicated and time-consuming intravenous drip, for example, bolus intravenous administration.

In order to meet such desire, the present inventors proposed a polymeric metal complex micelle obtained by forming a complex of poly(ethylene glycol)-poly($\alpha$,$\beta$-aspartic acid) (hereinafter abbreviated as PEG-P(Asp)) with CDDP in an aqueous medium (for example, Yokoyama; Kataoka et al., J. Controlled Release 39 (1996) 351–356; Nishiyama; Kataoka et al., Langmuir 1999, 15, 377–383). The above polymeric metal complex micelle maintains a stable micelle structure in refined water over a long period of time and slowly releases a Pt (II) complex in a physiological salt solution (0.15M NaCl solution) of 37° C., and it can maintain a polymer micelle structure over a period of about 10 hours. That is, attentions have to be paid to this metal complex micelle in the point that it can be present under physiological environment, for example, in blood circulation over a considerably long period of time. Further, it is indicated that when carrying out intravenous administration, the above metal complex micelle provides a carcinostatic effect and a nephrotoxicity-reducing effect which are excellent as compared with those of a CDDP simple substance (for example, Kataoka, PHARM TECH JAPAN Vol. 16, No. 8 (2000) 1209 to 1219).

However, desire to development of a pharmaceutical preparation which can maintain, if possible, a polymer micelle form under physiological environment over further longer period of time shall still be present. Accordingly, an object of the present invention is to provide a polymeric metal complex which can maintain a polymer micelle form under physiological environment over further longer period of time than the foregoing polymeric metal complex micelle of PEG-P(Asp) with CDDP.

DISCLOSURE OF THE INVENTION

In general, when a metal complex is stabilized, it is a usual case that metal remains unreleased from the complex formed or is not released efficiently or at a suitable speed. For example, if a chlorine ion ligand of CDDP is replaced with side chain residues (they have far stronger nucleophilicity as compared with that of a carboxyl anion) of cysteine, methionine and histidine contained in protein, a very stable complex is formed and is not replaced again with the chlorine ion ligand even in a physiological salt solution, and CDDP comes to show no activity in an organism in a certain case. Accordingly, the present inventors have investigated to develop a carrier having a ligand which can suitably be replaced with a chlorine ion ligand of CDDP. As a result thereof, it has been found that to be unexpected, a complex of a block copolymer comprising a poly(ethylene glycol) segment and a poly($\alpha$-glutamic acid) segment with CDDP has a characteristic which meets the object of the present invention, though it has on a side chain, a carboxyl anion (—COO$^-$) common to PEG-P(Asp) as a ligand which can be replaced with a chlorine ion of CDDP.

Hence, according to the present invention, provided is a complex which originates in a block copolymer represented by the following Formula I or II and cisplatin and in which an equivalent ratio (Pt/COO$^-$) of Pt in cisplatin to a carboxyl anion of the above copolymer is 0.3 or more, preferably 0.5 or more:

in Formula I and II described above, $R_1$ represents independently a hydrogen atom or an alkyl group which may be substituted with a functional group; A represents independently NH, CO or $R_5(CH_2)_p R_6$, in which $R_5$ is O, OCO, OCONH, NHCO, NHCOO, NHCONH, CONH or COO; $R_6$ is NH or CO; and p is an integer of 1 to 6; $R_2$ represents independently a hydrogen atom or an alkyl group or an aralkyl group; $R_3$ represents independently a hydrogen atom or a hydrophobic residue; m is independently an integer of 50 to 5000, preferably 100 to 1000; and n is independently an integer of 5 to 1000, preferably 10 to 500.

The present invention provides as well, as one more embodiment, a medicine, particularly a carcinostatic agent comprising the complex described above as an effective ingredient.

BEST MODE FOR CARRYING OUT THE INVENTION

The complex referred to in the present invention means a so-called coordinate compound in which one or both of two chlorine ions in a CDDP molecule are replaced with a carboxyl anion of the above block copolymer, but it shall not necessarily be restricted to a complex in which all of CDDP molecules form a coordinate bond with the above block copolymer. In other words, a part of the CDDP molecules may be carried on the above block copolymer by virtue of any physical bond other than a coordinate bond. However, preferred is a complex in which all of the CDDP molecules carried are coordinately bonded with the carboxyl groups of the above block copolymer in one or both of two chlorine ions in the CDDP molecule.

The term "cisplatin (or CDDP)" in "originating in and cisplatin (or CDDP)", "cisplatin (or CDDP)-encapsulating" and "encapsulated cisplatin (or CDDP)" described in the present specification does not necessarily mean a substance having the following structural formula:

and it is used in the meaning that a substance which stays in the state that one or two chlorine ions (Cl⁻) are eliminated from the above tissue is included therein.

The "polymer micelle" referred to in the present specification has a meaning usually used in the technical field concerned, and to be specific, it means a structural substance of a core-shell type comprising a shell (outer shell) comprising a PEG segment and a core (inner core) comprising a P(Asp) or P(Glu) segment in the block copolymer described above. According to the present invention, the polymer micelle shall not be restricted and means, to be specific, a substance formed by allowing the block copolymer to be autonomously subjected to multimolecular association in an aqueous medium in the coexistence of CDDP.

The block copolymer used in the present invention may be any copolymer as long as it is represented by Formula I or II described above and meets the object of the present invention. These copolymers can be produced by partially hydrolyzing a benzyl group of a block copolymer comprising a poly(ethylene glycol) segment and poly(γ-benzyl α-glutamate) segment as described in, for example, U.S. Pat. No. 2,777,530 (or U.S. Pat. No. 5,449,513) or partially hydrolyzing it after transesterification or substantially completely hydrolyzing it and partially esterifying, if necessary, a carboxyl group.

The functional group in the case where $R_1$ is an alkyl group which may be substituted with a functional group in Formula I and II usually can include a hydroxyl group which may be protected by one suitable protective group, for example, acetal or an aldehyde group, an amino group, a mercapto group and a sugar residue which may be reduced to ketal. The alkyl group which may have such functional group includes an alkyl group having 1 to 20 carbon atoms and can include preferably a linear or branched lower alkyl group such as 1 to 6 methyl, ethyl, propyl, butyl, hexyl, i-propyl and sec-butyl. The block copolymer of Formula I or II having such $R_1$ can be produced by preparing a corresponding PEG segment by a method described in, for example, WO96/33233, WO97/06202 and WO96/32434, then converting, for example, a ω-terminal thereof to an amino group and using this as an initiator to polymerize γ-benzyl glutamate N-carboxylic anhydride. A γ-benzyl group (corresponding to $R_2$) of the block copolymer thus obtained may be, as described above, partially hydrolyzed and/or transesterified or eliminated by substantially complete hydrolysis, and the alkyl group and the aralkyl group (a benzyl group and a phenethyl group) described above may partially be introduced thereinto in a certain case. The term "substantially complete hydrolysis" means that the case where at least 95%, preferably 99% of an ester group is eliminated is included therein, and 100% of an ester group is particularly preferably eliminated for the object of the present invention. When an alkyl group or an aralkyl group is introduced after partially hydrolysis or complete hydrolysis ($R_2$ is other than a hydrogen atom), up to 70%, preferably 50% and more preferably 30% of an ester group can be present.

In this case, it corresponds to a copolymer represented by Formula I-a in which A in Formula I represents NH:

wherein $R_1$, $R_2$, $R_3$, m and n are synonymous with those defined in Formula I.

A in Formula I or II can be changed, as described above, by a method for changing the ω-terminal in the PEG segment or a method for connecting the PEG segment with the P(Glu) segment, and it can represent, in addition to NH shown in Formula I-a, CO or $R_5(CH_2)_pR_5$ (wherein $R_5$ is O, OCO, OCONH, NHCO, NHCOO, NHCONH, CONH or COO; $R_6$ is NH or CO; and p is an integer of 1 to 6).

$R_3$ in Formula I or II is a hydrogen atom or a hydrophobic residue. The hydrophobic residue in the case of, for example, Formula I and Formula II can include respectively $C_{8-16}$ alkylcarbonyl and $C_{8-16}$ alkyl, phenylacetyl and benzyl, diphenylacetyl and benzhydryl, pyrenesulfonyl and pyrenyl, adamantyl and cholesteryl, but it shall not be restricted to them. These residues can be introduced by an acid chloride method and in addition thereto, an active esterification method. Such hydrophobic residues can be useful in a certain case for elevating a self association ability of the complex according to the present invention in an aqueous medium.

The term m in Formula I or II is an integer of 50 to 5000, preferably 100 to 1000, and n is an integer of 5 to 1000, preferably 10 to 500. The numbers of these m and n can be changed according to the presence or absence or a presence proportion of the groups other than a hydrogen atom as $R_2$ and $R_3$ in Formula I or II, and they are preferably those which can form a polymer micelle encapsulating a molecule or a part originating cisplatin (or encapsulating cisplatin) when the complex of the present invention is solubilized in water. For example, $R_2$ is benzyl, and in the case of such hydrophobic side chain, if remaining carboxylate is bonded to CDDP, a micelle is formed, so that an optional introducing rate can be set.

Further, in the complex according to the present invention, it is preferably observed by measurement of static light scattering that the polymer micelle described above is stably present in purified water of 37° C. and that the micelle form is maintained in a physiological salt solution (0.15M NaCl solution) for at least about 15 hours. The term "stably present in purified water" means that when the polymer micelle is dispersed or dissolved in purified water, CDDP substantially encapsulated therein is not released from the polymer micelle into water for at least two days. In the complexes described in examples mentioned later, CDDP was not observed to be released into water even after exceeding 80 hours. Further, it is confirmed that the micelle was stable over a period of several months or longer. On the other hand, the fact that it is observed by measurement of static light scattering to maintain a micelle form in a physiological salt solution is based on that in general, it is known that an intensity of scattered light in static light scattering (SLS) reflects an apparent weight average molecular weight of a polymer, and therefore a change in an apparent molecular weight of a polymer micelle can be evaluated from a change in an intensity of scattered light in SLS. For example, it is estimated that a fixed CDDP-encapsulating PEG-P(Asp) micelle maintains an apparent molecular weight thereof in a physiological salt solution of 37° C. for about 10 hours and that it is then dissociated, but in the PEG-P(Glu) micelle according to the present invention, an apparent molecular weight of the polymer micelle is maintained (that is, the micelle form is maintained) for about 15 hours. Further, in the polymer micelle according to the present invention, an apparent molecular weight of the polymer micelle is maintained preferably over a period of about 20 hours.

Further, the polymer micelle according to the present invention has a cumulant particle diameter of about 15 to about 500 nm, preferably about 20 to about 200 nm obtained by measurement of dynamic light scattering (DLS) in an aqueous medium, and it can be a monodispersed micelle having a narrow particle size distribution.

In CDDP encapsulated in such polymer micelle, an equivalent ratio (Pt/COO⁻) of Pt contained in CDDP to a carboxyl anion contained in the copolymer is 0.3 or more, preferably 0.5 or more. If this value is less than 0.3, the stable polymer micelle can not usually be formed in water in a certain case. The higher this value, the better as long as the polymer micelle is stable, and it is usually 2 or less. In general, a polymer micelle has a critical association concentration (c. a. c), and the CDDP-encapsulating micelle according to the present invention is very stable as well against dilution.

On the other hand, it shall not theoretically be restricted, and the above CDDP-encapsulating micelle slowly releases CDDP in a physiological salt solution of 37° C. which is close to a physiological condition while accompanied with a replacement of a ligand (COO⁻→Cl⁻) of a Pt(II) complex, and the micelle form is decayed after about 15 hours pass as described above. It is estimated that in such CDDP-encapsulating micelle, a shell (outer shell) has a tissue in which several ten to several hundred pieces of the flexible and hydrophilic PEG segments are close together and come out from an interface to a core (inner core) in a brush shape. Furthermore, it falls in a mesoscopic size range (a level of 20 to 100 nm), and therefore capable of being prevented is non-specific incorporation by reticuloendothelial system (RES) represented by a Kupffer cell of a liver. In addition thereto, filtration by glomerule can be prevented, and therefore it is estimated that the above CDDP-encapsulating micelle can be circulated in a blood flow in a micelle form over 15 hours. Then, free or substantially free CDDP can be released in a tumor part for short time. Further, the CDDP-encapsulating micelle is low in toxicity such as nephrotoxicity similarly to CDDP-encapsulating PEG-P(Asp) described in Kataoka, PHARM. TECH. JAPAN, Vol. 16, No. 8 (2000) 1209 to 1219.

Accordingly, the complex according to the present invention, to be more specific, the CDDP-encapsulating PEG-P (Glu) micelle can exhibit an antitumor activity with which a CDDP simple substance is intrinsically endowed in a new administration form. Thus, according to the present invention, a carcinostatic agent comprising the complex according to the present as an active ingredient is provided. Such carcinostatic agent is stored in a freeze dry form of the above CDDP-encapsulating PEG-P(Glu) micelle itself or, if necessary, together with a filler, for example, glucose, mannose and an oligomer or a stabilizer such as polyethylene glycol, and it can be administered by bolus intravenous administration using such diluent that an initial concentration of the drug is 0.1 to 10 mg/ml, for example, in the form of a sterile isotonic aqueous solution so that the dosage is usually 0.5 to 50 mg/kg of the body.

The CDDP-encapsulating PEG-P(Glu) micelle according to the present invention can be prepared in the same manner as that of PEG-P(Asp) described in Nishiyama et al. described above.

The present invention shall be explained below with reference to specific examples, but the present invention shall not be restricted to them.

EXAMPLE 1

In the present example, the production example of the CDDP-encapsulating polymer micelle of PEG-P(Glu) of the present invention shall be shown together with PEG-P(Asp) described in Nishiyama et al. described above. The block copolymer used in the present invention is shown by, for example, the following structural formula:

Cisplatin (CDDP) was dissolved in water (5 mmol/L). Dissolved in this solution ([CDDP]/[Asp or Glu]=1.0) were a polyethylene glycol-polyaspartic acid block copolymer (PEG-P(Asp)) and a polyethylene glycol-polyglutamic acid block copolymer (PEG-P(Glu)) (hereinafter, notation of the block copolymer in the examples shall be (molecular weight of PEG×10$^{-3}$)-(polymerization degree of polyamino acid); for example, PEG-P(Glu) 5–35 means that PEG has a molecular weight of about 5000 and (Glu) has a polymerization degree of about 35), and they were reacted at 37° C. for 72 hours. The resulting solution was refined by repeating ultrafiltration (fractionated molecular weight: 100,000).

Figure 1:
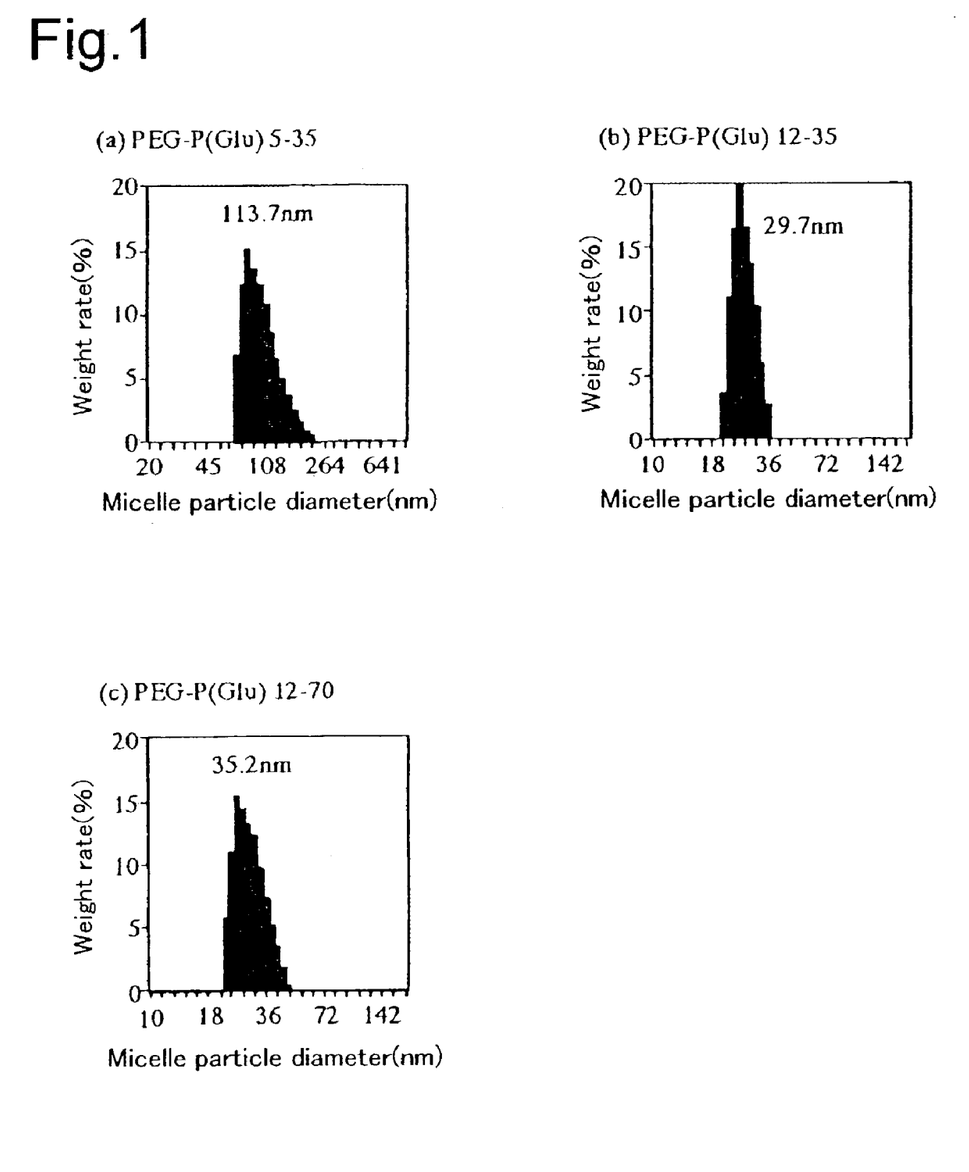
FIG. 1 is a graph showing a dispersibility obtained by measuring dynamic light scattering (DLS) of various CDDP-encapsulating PEG-P(Glu) prepared in Example 1 according to the present invention.

The particle diameter was measured (cumulant analysis) by dynamic light scattering (DLS), and the results thereof are shown in Table 1. It was confirmed from PEG-P(Asp) 5–40 and 5–79 that monodispersed particles having the particle diameters of 22.1 nm and 22.5 nm were formed respectively, and it was confirmed from PEG-P(Glu) 5–35, 5–70 and 12–70 that monodispersed particles having the particle diameters of 114 nm, 29.7 nm and 35.2 nm were formed respectively (refer to FIG. 1). In contrast with this, it was not confirmed at all from PEG-P(Asp) 12–29 that particles were formed. That is, the polymer micelle was increased in a particle diameter by changing a polyamino acid tissue constituting the polymer micelle inner core from aspartic acid (Asp) to more hydrophobic glutamic acid (Glu), and further, it became possible to prepare the polymer micelle comprising a copolymer containing PEG having a molecular weight of 12,000, which was difficult to prepare from Asp.

TABLE 1

Particle diameter measurement (cumulant analysis) by DLS

| | | Micelle particle diameter [nm] | Polydispersibility ($\mu_2/$ ) |
|---|---|---|---|
| PEG-P (Asp) | 5–40 | 22.1 | 0.146 |
| | 5–79 | 22.5 | 0.073 |
| PEG-P (Glu) | 5–35 | 126.7 | 0.077 |
| | 12–35 | 26.5 | 0.185 |
| | 12–70 | 35.2 | 0.078 |

EXAMPLE 2

Figure 2:
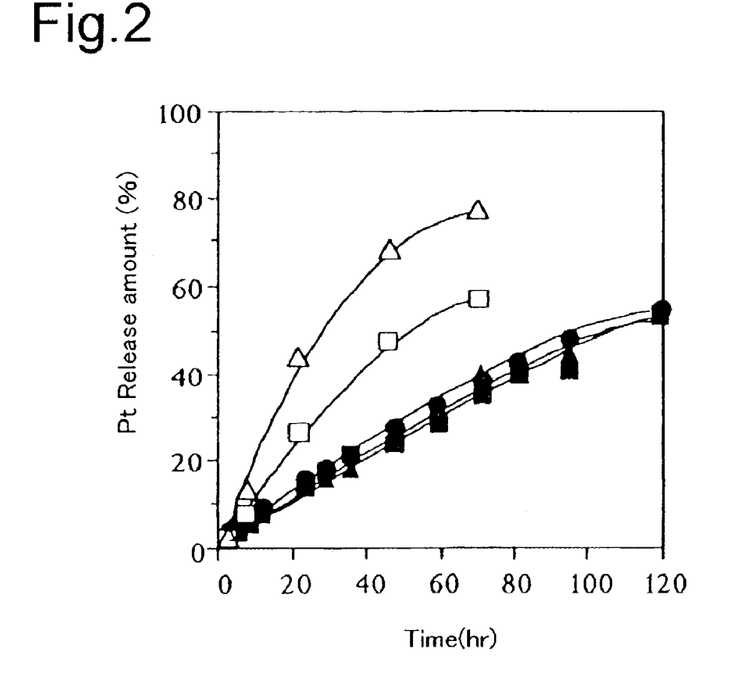
FIG. 2 is a graph showing a release behavior of CDDP(Pt) from a CDDP-encapsulating PEG-P(Glu) polymer micelle according to the present invention and a CDDP-encapsulating PEG-P(Asp) polymer micelle of comparison into a physiological salt solution. In the graph, Δ: PEG-P(Asp) 5–40; □: ditto 5–80; ●: PEG-P(Glu) 5–35; ▲: ditto 12–35; and ■: ditto 12–70.

Release behavior of CDDP in a physiological salt solution of 37° C., which came from a polymer micelle encapsulating CDDP obtained in Example 1 was evaluated by dialysis (fractionated molecular weight of dialysis membrane: 1,000). A dialysis membrane having a fractionated molecular weight of 1,000 was used to carry out dialysis for a physiological salt solution of 50 times, and an amount of platinum (Pt) contained in the outer liquid obtained after a fixed time was determined by flameless atomic absorption. It was confirmed that a release speed of CDDP from the polymer micelle was inhibited to a large extent by changing the structure of an amino acid constituting the micelle from Asp to Glu (refer to FIG. 2). Further, CDDP was not observed to be released from the micelle in water.

EXAMPLE 3

Figure 3:
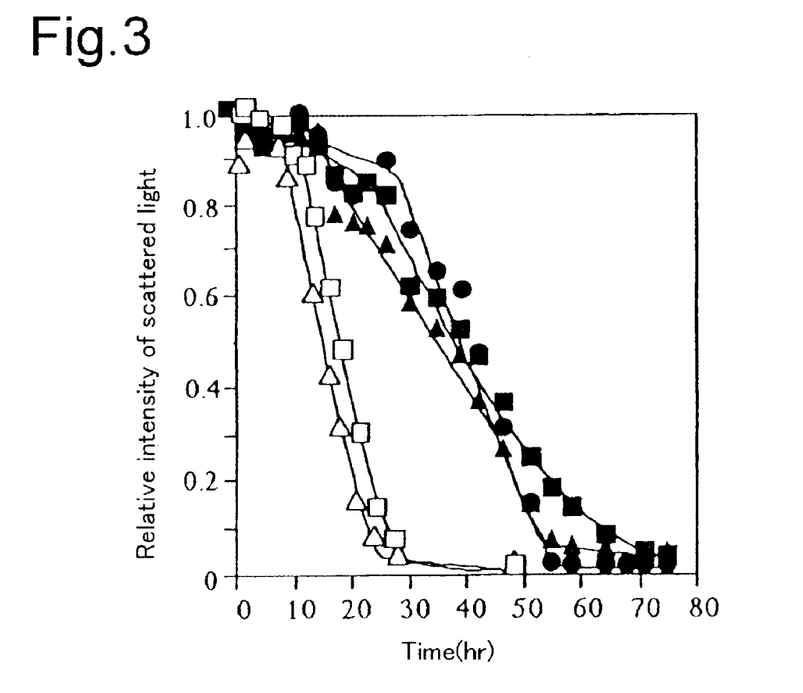
FIG. 3 is a graph showing a change in a relative intensity of scattered light in static light scattering (SLS) with the passage of time for evaluating stability of a CDDP-encapsulating PEG-P(Glu) polymer micelle according to the present invention and a CDDP-encapsulating PEG-P(Asp) polymer micelle of comparison in a physiological salt solution. Signals in the graph are the same as in FIG. 2.

The stability of the particles in the polymer micelle obtained in Example 1 in a physiological salt solution of 37° C. was evaluated by a change in a relative intensity of scattered light in static light scattering (SLS). In general, it is known that an intensity of scattered light in SLS reflects an apparent weight average molecular weight of a particle. It was confirmed that the micelle showed non-linear dissociation behavior in a physiological salt solution of 37° C. and that it was slowly dissociated after maintaining an apparent molecular weight thereof for a fixed time. Further, it was confirmed that time for which an apparent molecular weight of the micelle was maintained was extended to a large extent from about 10 hours to about 30 hours by changing the structure of an amino acid in the inner core of the micelle from Asp to Glu (refer to FIG. 3).

EXAMPLE 4

Figure 4:
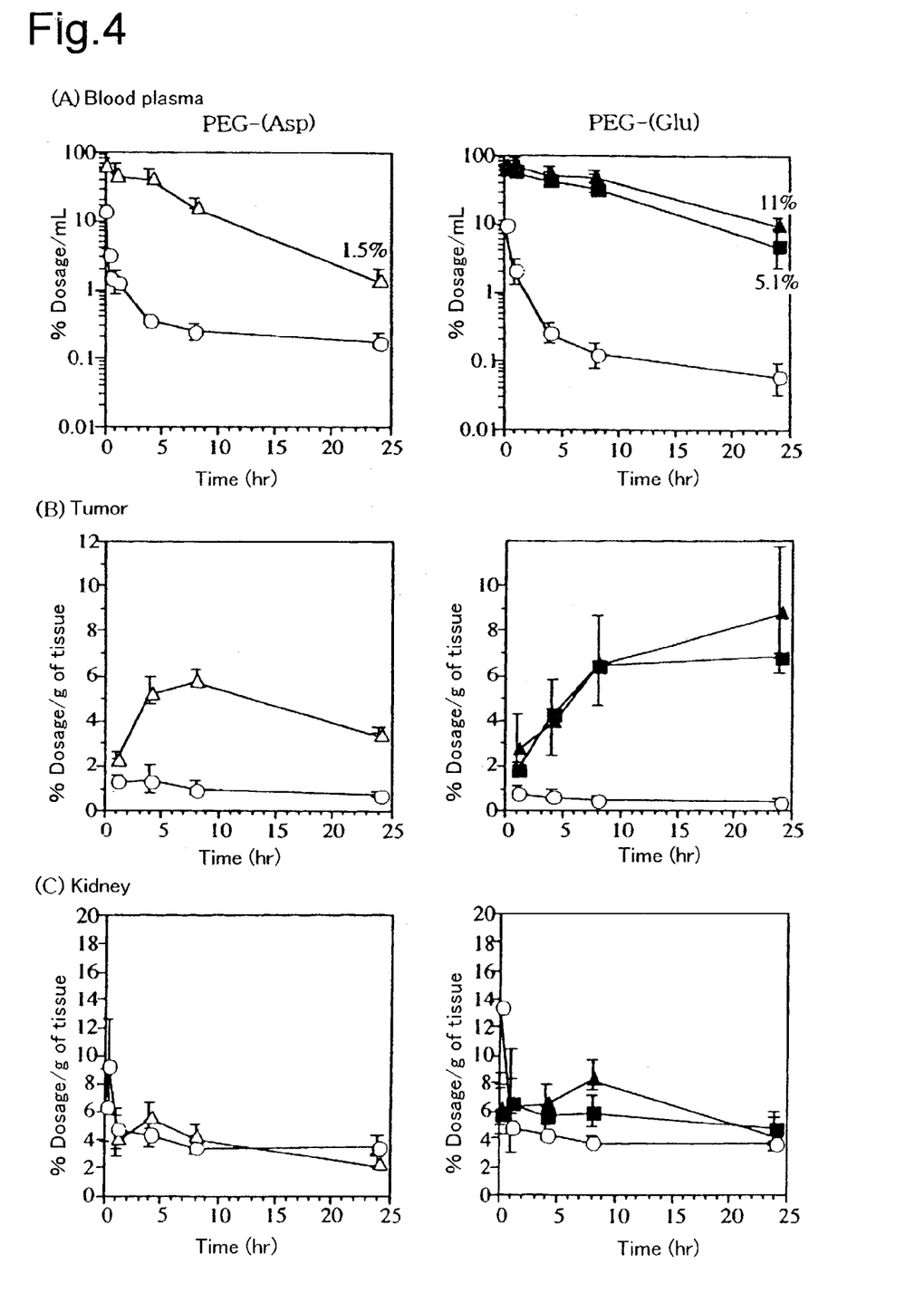
FIG. 4 is a graph showing respectively results obtained by evaluating a change in a blood plasma platinum concentration (4(A)) and a change with the passage of time (4(B) to (E)) in accumulation of platinum in the principal organs observed when free CDDP and the CDDP-encapsulating micelles are administered from a caudate vein according to Example 4. In the graph, ○: free CDDP; Δ: PEG-P(Asp) 5–40; ▲: PEG-P(Glu) 12–35; and ■: ditto 12–70.

Evaluated were a change in a blood plasma platinum concentration and a change with the passage of time in accumulation of platinum in the principal organs observed when free CDDP and the CDDP-encapsulating micelle were administered from a caudate vein to a C57BL6/N mouse (n=4, male, 6 ages in week) in which Louis pulmonary cancer was subcutaneously transplanted to a hypogastric region, and the results thereof are shown in FIG. 4. In the graph, ○: free CDDP; Δ: PEG-P(Asp) 5–40; ▲: PEG-P (Glu) 12–35; and ■: ditto 12–70.

In a change with the passage of time in the blood plasma platinum concentration (FIG. 4(A)), it was confirmed that the CDDP-encapsulating micelle had a blood plasma retentivity which was extended to a large extent as compared with that of free CDDP. In a CDDP-encapsulating micelle-administered group formed from PEG-P(Asp) 5–40, the blood plasma platinum concentration was maintained to a high value (45% dosage/mL) until 4 hours passed after administration and then quickly reduced, and it reached to 1.5% dosage/mL after 24 hours. In contrast with this, in the CDDP-encapsulating micelle-administered groups formed from PEG-P(Glu) 12–35 and ditto 12–70, the blood plasma platinum concentration was maintained to a high value (57 and 34% dosage/mL respectively) until 8 hours passed after administration and then slowly reduced, and the values after 24 hours were 11 and 5.1% dosage/mL respectively. It is considered that these results are not inconsistent with non-linear decay behavior of the micelle versus time notably delayed by changing the structure of an amino acid in the inner core of the micelle from Asp to Glu which was observed in a physiological salt solution of 37° C. (refer to FIG. 3). Accordingly, a blood plasma retention time of the CDDP-encapsulating micelle was extended to a large extent by changing the structure of an amino acid in the inner core of the micelle from Asp to Glu.

In accumulation (FIG. 4(B)) of platinum in a tumor, it was confirmed that the CDDP-encapsulating micelle was effectively accumulated as compared with free CDDP. In the CDDP-encapsulating micelle-administered group formed from PEG-P(Asp) 5–40, the tumor platinum concentration was effectively increased until 4 hours passed after administration in which the high blood plasma platinum concentration was observed, but it then reached the peak, and the value observed after 24 hours passed since administered was 4.8 times as large as the value of free CDDP. In contrast with this, in the CDDP-encapsulating micelle-administered groups formed from PEG-P(Glu) 12–35 and ditto 12–70, the blood plasma platinum concentration was effectively increased until 8 hours passed after administration, and the values observed after 24 hours passed since administered were 20 times and 15 times as large as the value of free CDDP respectively. Thus, a tumor accumulativeness of the CDDP-encapsulating micelle was elevated to a large extent by changing the structure of an amino acid in the inner core of the micelle from Asp to Glu.

In accumulation (FIG. 4(C)) of platinum in a kidney, it was confirmed that the CDDP-encapsulating micelle effectively inhibited high accumulation immediately after administration (about 15 minutes) which was observed in free CDDP. It is reported in literatures that accumulation of CDDP exceeding some threshold level brings about nephrotoxicity, and the CDDP-encapsulating micelle is expected to effectively inhibit nephrotoxicity by avoiding high accumulation in a kidney immediately after administration. It was confirmed that though the CDDP-encapsulating micelle formed from PEG-P(Glu) showed an extended blood plasma retentivity and a high tumor accumulativeness as compared with those of the CDDP-encapsulating micelle formed from PEG-P(Asp) (FIGS. 4(A) and (B)), it had only the same level of accumulativeness in a kidney which was a by-effected organ of CDDP.

In accumulation (FIGS. 4(D) and (E)) of platinum in a liver and a spleen, it was confirmed that the CDDP-encapsulating micelle formed from PEG-P(Asp) 5–40 showed quick and high accumulation in a liver and a spleen after 8 hours passed since administered in which the blood plasma platinum concentration was suddenly decreased, but the micelle formed from PEG-P(Glu) did not show such sudden accumulation in a liver and a spleen and that particularly in the micelle formed from PEG-P(Glu) 12–35, accumulation of platinum in a liver was effectively inhibited.

An area under the curve (AUC) was calculated from a tissue platinum concentration-time curve of free CDDP and the CDDP-encapsulating micelle in FIG. 4 to determine a ratio of AUC of each organ to that of a tumor, and the results thereof are shown in Table 2. Free CDDP shows a value of 1 or more in kidney AUC/tumor AUC and liver AUC/tumor AUC and is considered to have a higher specificity to a kidney and a liver than to a tumor. On the other hand, the CDDP-encapsulating micelle formed from PEG-P(Asp) 5–40 shows a value of 1 or more in liver AUC/tumor AUC and spleen AUC/tumor AUC and is considered to have a higher specificity to a liver and a spleen than to a tumor. In contrast with this, the micelle formed from PEG-P(Glu) 12–35 shows a value of 1 or less in all tissues AUC/tumor AUC and is considered to have a high specificity to a tumor.

TABLE 2

Ratio (0–24 hours) of each tissue AUC to tumor AUC

|  | CDDP | PEG-P (Asp) 5–40 | CDDP | PEG-P (Glu) 12–35 |
|---|---|---|---|---|
| Kidney AUC/tumor AUC | 3.9 | 0.84 | 7.7 | 1.0 |
| Liver AUC/tumor AUC | 2.6 | 2.3 | 2.7 | 0.77 |
| Spleen AUC/tumor AUC | 0.31 | 1.2 | 0.43 | 0.67 |
| Muscle AUC/tumor AUC | 0.13 | 0.055 | 0.17 | 0.052 |

EXAMPLE 5

Figure 5:
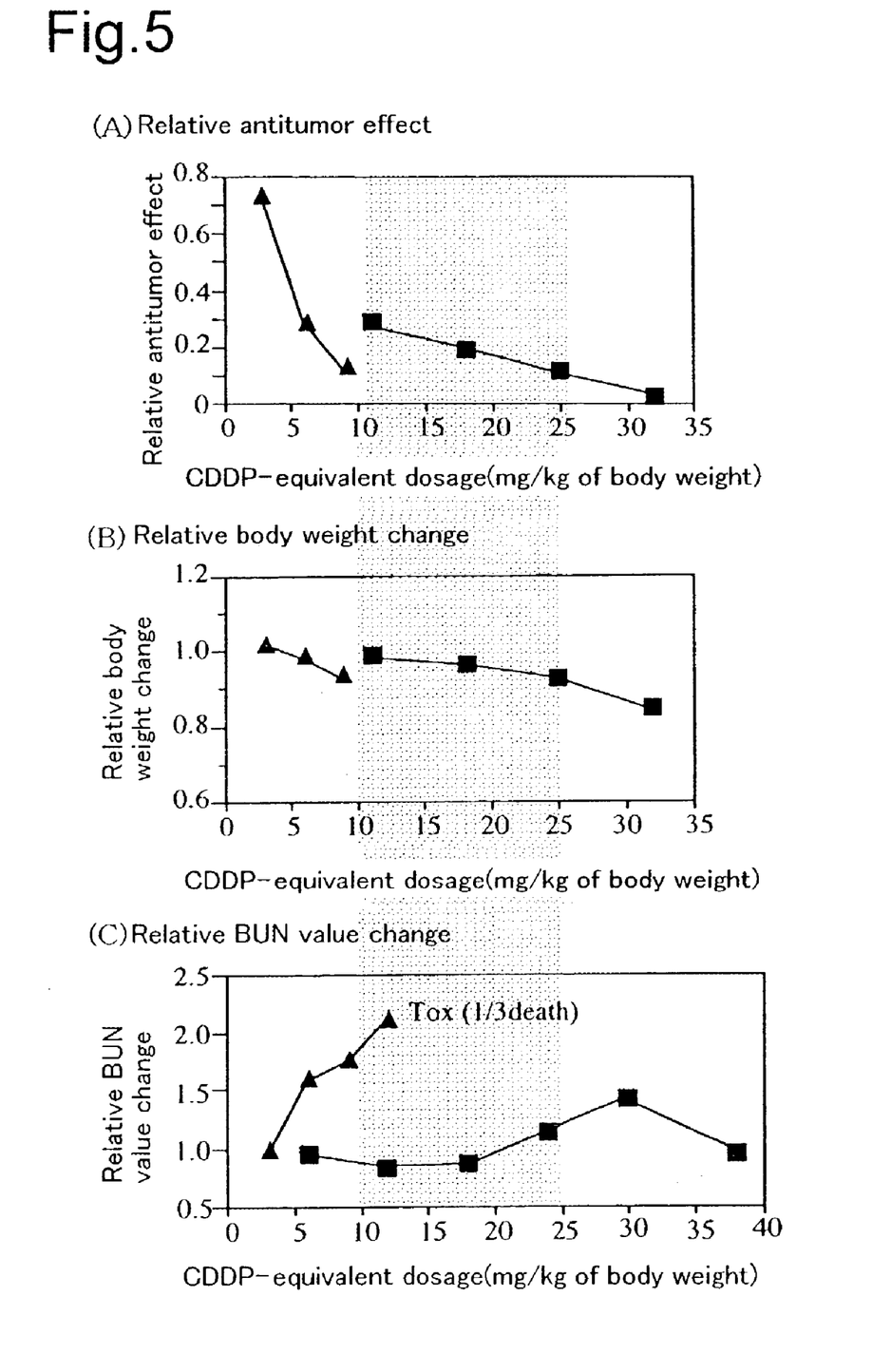
FIG. 5 is a graph showing respectively results obtained by evaluating an antitumor effect (5(A)) of a mouse to a CDDP-equivalent dosage observed when a CDDP-encapsulating micelle formed from free CDDP or PEG-P(Glu) 12–35 is administered once from a caudate vein according to Example 5, a change in the body (5(B)) and a change in a relative BUN value (5(C)) (▲: free CDDP; and ■: PEG-P(Glu) 12–35).

Evaluated were an antitumor effect of the mouse to a CDDP-equivalent dosage and a weight change observed when free CDDP or the CDDP-encapsulating micelle formed from PEG-P(Glu) 12–35 was administered once from a caudate vein to a C57BL6/N mouse (n=4, male, 6 ages in week) in which Louis pulmonary cancer was subcutaneously transplanted to a hypogastric region, and the results thereof are shown in FIGS. 5(A) and (B) respectively (▲: free CDDP; and ■: micelle formed from PEG-P(Glu) 12–35). In FIG. 5, calculated were duration integrations (up to 17 days since drug treatment) of relative values in a change in a tumor volume and a weight change on a zero day, and the ratios of the drug-treated group to the drug-non-treat group in the values were shown as an antitumor effect and a weight change respectively. Further, the drug was administered once from a caudate vein to a normal C57BL6/N mouse (n=4, male, 6 ages in week) to evaluate a urea nitrogen (BUN) value in blood plasma after 6 days. It is generally known that an increase in a BUN value is an index for nephrotoxicity. The ratio of the drug-treated group to the drug-non-treat group in this BUN value was calculated as well, and the relative BUN value to the CDDP-equivalent dosage was shown in FIG. 5(C). As a result thereof, an increase in the antitumor effect, a reduction in the weight and a rise in the BUN value were confirmed dependently on the dosage in free CDDP (one mouse out of 3 mice treated at 12 mg/kg was toxically died). In contrast with this, confirmed in the CDDP-encapsulating micelle was a drug dosage area (11 to 25 mg/kg) in which the high antitumor effect was obtained without having a reduction in the weight and a rise in the BUN value to a large extent. It is considered that an expansion in the effective therapeutic area of CDDP caused by such reduction to the polymer micelle was brought about by selective accumulation of CDDP in a tumor caused by reduction to the micelle shown in Example 4.

INDUSTRIAL APPLICABILITY

The CDDP-encapsulating micelle according to the present invention is a CDDP pharmaceutical preparation of a new type showing decay behavior which is controlled with time and effectively accumulated in a solid cancer to show a very high carcinostatic effect. On the other hand, it markedly reduces nephrotoxicity which is the largest problem in administering CDDP. Further, the encapsulation by using a polymer micelle rapidly raises a solubility of scarcely soluble CDDP in water and makes it possible to easily administer CDDP without making hydration which is considered not preferred in terms of QOL of a patient. Thus, the CDDP-encapsulating micelle is considered to have a lot of advantages in terms of medical practice. Accordingly, it can be used in the medical service and the medicinal production industry.

The invention claimed is:

1. A complex which comprises a block copolymer represented by Formula I or II:

-continued

II wherein in Formula I and II, $R_1$ represents independently a hydrogen atom, a $C_{1-20}$ alkyl group or a $C_{1-20}$ alkyl group substituted with one or two substituents selected from the group consisting of acetal, hydroxyl, aldehyde, amino and mercapto; A represents independently NH, CO or $R_5(CH_2)_p R_6$, in which $R_5$ is O, OCO, OCONH, NHCO, NHCOO, NHCONH, CONH or COO; $R_6$ is NH or CO; and p is an integer of 1 to 6; $R_2$ represents independently a hydrogen atom or an alkyl group or an aralkyl group, provided that a hydrogen atom accounts for 95% or more of all $R_2$; $R_3$ represents independently a hydrogen atom or in the case of Formula I, $R_3$ is $C_{8-16}$ alkylcarbonyl, phenylacetyl, diphenylacetyl or pyrenesulfonyl, and in the case of Formula II, $R_3$ is $C_{8-16}$ alkyl, benzyl, benzhydryl, adamantyl or cholesteryl; m is independently an integer of 50 to 5000; and n is independently an integer of 5 to 500; and cisplatin, wherein one or two chlorine ions in the cisplatin are replaced with the carboxyl anion of the block copolymer.

2. The complex as described in claim 1, wherein $R_2$ is a hydrogen atom or a benzyl group.

3. The complex as described in claim 1, wherein the block copolymer is a block copolymer represented by Formula I-a:

I-a wherein $R_1$, $R_2$, $R_3$, m and n have the same meanings as defined in claim 1.

4. The complex as described in claim 3, wherein $R_1$ is a hydrogen atom, a $C_{1-6}$ aklyl group, or a $C_{1-6}$ alkyl group substituted with one substituent selected from the group consisting of acetal, hydroxyl, amino and mercapto; $R_2$ is a hydrogen atom or benzyl; and $R_3$ is a hydrogen atom.

5. The complex as described in claim 1, which is a polymer micelle.

6. The complex as described in claim 5, wherein it is observed by measurement of static light scattering that the polymer micelle is stably present in purified water of 37° C. and that the micelle form is maintained in a physiological salt solution (0.15M NaCl solution) for at least about 15 hours.

7. A medicinal preparation comprising a medicinally effective amount of a complex which comprises a block copolymer represented by Formula I or II:

I

-continued

II wherein in Formula I and II, $R_1$ represents independently a hydrogen atoms, a $C_{1-20}$ alkyl group or a $C_{1-20}$ alkyl group substituted with one or two substituents selected from the group consisting of acetal, hydroxyl, aldehyde, amino and mercapto; A represents independently NH, CO or $R_5(CH_2)_p R_6$, in which $R_5$ is O, OCO, OCONH, NHCO, NHCOO, NHCONH, CONH or COO; $R_6$ is NH or CO; and p is an integer of 1 to 6; $R_2$ represents independently a hydrogen atom or an alkyl group or an axailcyl group, provided that a hydrogen atom accounts for 95% or more of all $R_2$; $R_3$ represents independently a hydrogen atom or in the case of Formula I, $R_3$ is $C_{8-16}$ alkylcarbonyl, phenylacetyl, diphenylacetyl or pyrenesulfonyl, and in the case of Formula II $R_3$ is $C_{8-16}$ alkyl, benzyl, benzhvdryl, adamantyl or cholesteryl; in is independently an integer of 50 to 5000; and n is independently an integer of 5 to 500; and cisplatin, wherein one or two chlorine ions in the cisplatin are replaced with the carboxyl anion of the block copolymer; together with a filler or a diluent.

8. The medicinal preparation as described in claim 7, being a carcinostatic agent.

9. The medicinal preparation as described in claim 7, having a dosage form of 0.5 to 50 mg/kg for intravenous administration.

10. A therapeutic method of treatment of pulmonary cancer comprising administering an effective amount of the medicinal preparation as described in claim 7 to a patient in need thereof.

11. The therapeutic method as described in claim 10, wherein the medicinal preparation is administered in an amount of 0.5 to 50 mg/kg of body weight by intravenous administration.

12. A method for preparing a carcinostatic agent, which comprises a step of forming the complex according to claim 1 into a polymer micelle.

13. The complex as described in claim 1, wherein the complex maintains an apparent molecular weight of a polymer micelle comprising the complex in a physiological salt solution of 37° C. for at least about 15 hours and then is slowly dissociated.

14. The complex as described in claim 13, wherein the complex maintains an apparent molecular weight of the polymer micelle comprising the complex for at least about 20 hours and then is slowly dissociated.

15. The complex as described in claim 13, wherein the polymer micelle has an average diameter size of 20 to 100 nm.

16. The medicinal preparation as described in claim 7, wherein the complex maintains an apparent molecular weight of a polymer micelle comprising the complex in a physiological salt solution of 37° C. for at least about 15 hours and then is slowly dissociated.

17. The medicinal preparation as described in claim 16, wherein the polymer micelle has an average diameter size of 20 to 100 nm.

18. The method as described in claim 12, wherein the complex as described in claim 1 maintains an apparent molecular weight of a polymer micelle comprising the complex in a physiological salt solution of 37° C. for at least about 15 hours and then is slowly dissociated.

19. The method as described in claim 18, wherein the polymer micelle has an average diameter size of 20 to 100 nm.

20. The complex as described in claim 1, which an equivalent ratio (Pt/COO$^-$) of Pt in the cisplatin to the carboxyl anion of the block copolymer is 0.3 or more.

21. The medicinal preparation as described in claim 7, in which an equivalent ratio (Pt/COO$^-$) of Pt in the cisplatin to the carboxyl anion of the block copolyiner is 0.3 or more.

* * * * *